_United States Patent_ [19]

Nagai et al.

[11] 3,946,105

[45] Mar. 23, 1976

[54] PREPARATION OF ANTI-α1-FETOGLOBULIN

[75] Inventors: Hidetaka Nagai, Hachioji; Eiichi Sato, Funabashi; Fujio Kobayashi, Higashimurayama, all of Japan

[73] Assignee: Kowa Company, Ltd., Nagoya, Japan

[22] Filed: Feb. 22, 1973

[21] Appl. No.: 334,877

Related U.S. Application Data

[62] Division of Ser. No. 99,312, Dec. 17, 1970, Pat. No. 3,819,822.

[30] Foreign Application Priority Data

Dec. 18, 1969 Japan.............................. 44-101870
Feb. 19, 1970 Japan.............................. 45-14335
July 29, 1970 Japan.............................. 45-66238
Aug. 28, 1970 Japan.............................. 45-75452

[52] U.S. Cl.................. 424/12; 260/112 B; 424/85; 424/88
[51] Int. Cl.² A23J 1/06; B01D 13/00; B01D 15/08; G01N 1/00
[58] Field of Search............. 424/12, 85; 260/112 R, 260/112 B

[56] References Cited

UNITED STATES PATENTS

| | | | |
|---|---|---|---|
| 3,128,228 | 4/1964 | Michl.......................... | 260/112 B X |
| 3,301,842 | 1/1967 | Schultze......................... | 260/112 R |
| 3,449,316 | 6/1969 | Querry........................... | 260/112 R |

OTHER PUBLICATIONS

Alpert, N.E. J. Med., Vol. 278, 1968, pp. 984–986.
Gitlin, J. of Clin. Invst., Vol. 45, 1966, pp. 1826–1837.
Uriel, C. R. Acad. Sci. Paris, Vol. 265, Series D, 3 July 1967, pp. 75–78.
Spiro, J. Biol. Chem., Vol. 235, Oct. 1960, pp. 2860–2869.

_Primary Examiner_—Albert T. Meyers
_Assistant Examiner_—A. P. Fagelson
_Attorney, Agent, or Firm_—Oblon, Fisher, Spivak, McClelland & Maier

[57] ABSTRACT

A diagnostic agent for primary hepatoma which has anti-α1-fetoglobulin, and a process for the preparation of the diagnostic agent for primary hepatoma which comprises the steps of dissolving the anti-α1-fetoglobulin together with a support medium and allowing the same to solidify in a diffused condition.

4 Claims, No Drawings

PREPARATION OF ANTI-α1-FETOGLOBULIN

This is a division of application Ser. No. 99,312, filed Dec. 17, 1970, now U.S. Pat. No. 3,819,822.

BACKGROUND OF THE INVENTION

The instant invention relates to diagnostic agents which are highly useful and highly sensitive for the clinical diagnosis of primary hepatoma as distinguished from metastatic and other liver disease. More particularly, the invention relates to new serological diagnostic agents for the determination of primary hepatoma, which are based on anti-α1-fetoglobulin. This invention also relates to methods for the preparation of said serological diagnostic agents. Furthermore, this invention relates to diagnostic methods which depend upon the use of said diagnostic agent.

Originally, it was found that the serum of the cattle fetus contained a type of α1-globulin which was designated α1-fetoglobulin (Fetuin) [K. O. Pedersen, Nature 154, 575 (1944)]. It was then discovered that this particular substance also occurred in the sera of fetuses of different animal species and was specific to various species. Those findings were followed by the discovery that the same substance also occurred in the serum of the human fetus, C. G. Bergstrand, et al., J. Clin. & Lab. Invest. 8 174 (1956). Recently, it was further demonstrated by immunological precipitin reactions, that α1-fetoglobulin occurs in the sera of patients having primary hepatoma [Yu. S. Tatarinov, Vop. Med. Khim. 11 (2) 20 (1965) and others ]. It has thus been suggested that the presence or absence of α1-fetoglobulin may provide a test for primary hepatoma. Over the succeeding years, we conducted extensive research into the basic mechanism of these cancers on the strength of the finding that metabolism of the human being afflicted with the cancerous diseases are analogous to that of the fetus, and that α1-fetoglobulin is closely related to primary hepatoma. Our effort has been largely concentrated on the development of improved diagnostic agents for clinical use.

SUMMARY OF THE INVENTION

The effort has now been repaid by the discovery of a quick and accurate method for the diagnosis and quantitative determination of those cancers, which do not involve the use of complicated chemical operations and costly, intricate equipment.

It is an object of this invention to provide a diagnostic agent which offers a high detection sensitivity for those diseases, a reduced incidence of doubtful positive results, and a high degree of quantitative reliability.

It is another object of the invention to provide a purified grade of anti-α1-fetoglobulin which is important in the preparation of the diagnostic agents of this invention.

It is still another object to provide a purified grade of α1-fetoglobulin which is important in the preparation of said diagnostic agent.

A significant feature of this invention resides in the use of anti-α1-fetoglobulin, i.e., an antibody which can be obtained either by (a) the immunization of animals with antigen derived with α1-fetoglobulin from the ascites or serum of a patient having a primary hepatoma, or (b) from the fetal serum, in the form of (1) a dispersed and solidified preparation which is obtainable by dissolving the anti-α1-fetoglobulin together with a support medium and allowing the same to coagulate, or (2) a dispersion which is obtainable by causing the anti-α1-fetoglobulin to be adsorbed onto a carrier medium and which is then dispersed in a dispersion medium.

Another important feature of this invention lies in the method used in the preparation of such a purified grade of anti-α1-fetoglobulin. Thus, the ascites or serum derived from a patient having a hepatoma or the serum of the human fetus is used to immunize an animal. A blood sample is taken from the animal. From this blood sample the serum is separated and the antiserum is absorbed with normal human serum, or with an insoluble immunoadsorbent, obtained by treating normal human serum with, for example, glutaraldehyde. Alternatively, the above ascites or serum is preliminarily purified by usual protein fractionation and the resulting α1-fetoglobulin fraction is used to immunize an animal. A blood sample is then taken from the animal and the serum is separated.

Another important feature of the invention lies in the method of preparing the purified grade of α1-fetoglobulin. The ascites or serum of a patient having a primary hepatoma is dialyzed against acrinol and precipitated. The dialyzate is purified by a protein fractionation technique.

Since the first suggestion was made, as mentioned above, that the presence or absence of α1-fetoglobulin might be used in the discriminatory diagnosis of hepatoma, a number of workers have attempted immunodiagnosis or primary hepatoma. To this day, however, no satisfactory diagnostic agent has been discovered, and, at present, the immunodiffusion and immuno-electrophoretic techniques, both being versatile methods useful in many immunodiagnostic applications, are being utilized by analogy. Immunodiffusion may be classified into single and double diffusion techniques. The single diffusion technique is a diagnostic method in which a tube containing the antigen, the antibody and diffusion medium in three distinct layers gives a precipitin band in the middle layer comprising said diffusion medium at the level corresponding to the optimum antigen-antibody ratio. This level is used as a diagnostic measure and is generally known as Oudin's method. The double diffusion technique, known as Ouchterlony's method, is such that the antibody is placed in a central well and the antigen is placed in a plurality of satellite wells, each of said wells having been bored in an agar layer on a plate. A precipitin ring appears in the position corresponding to the optimum antigen-antibody ratio, as has just been described above for the single diffusion technique, and their precipitin ring is used for diagnosis. Oudin's method, in which a precipitin ring is developed at a level which is determined by the diffusion coefficients and the concentrations of the antigen and antibody, is advantageous for the quantitation of the antigen. On the other hand, Ouchterlony's method proves more useful when it is used to discriminate between different antigens.

Immuno-electrophoresis is a combination of ordinary zone electrophoresis and the above-mentioned immunodiffusion. Thus, if the antibody is positioned in parallel with the direction of migration of the antigen, which has been linearly fractionated, a precipitin ring is developed in a location corresponding to the optimum ratio, as has been described above, and this precipitin ring is used as a diagnostic measure. This method is excellent in reproducibility.

However, those prior art diagnostic methods are different from the methods developed specifically for the discriminatory diagnosis of the subject disease of this invention, and although they may be used, each of those methods have many disadvantages. For instance, those methods are characterized by a high incidence of doubtful positive results. They require expensive equipment and involve complicated and time-consuming procedures which are incidental or essential to the necessary diagnosis. Thus, a more specific and simple method has been desired in order that a large number of patients may be diagnosed in a limited time.

The studies made by us in an effort to overcome those numerous disadvantages have led to the finding that by dissolving anti-$\alpha$1-fetoglobulin together with a support medium and allowing it to solidify in a dispersed state or causing anti-$\alpha$1-fetoglobulin to be adsorbed on a carrier medium and, as such, dispersed in a dispersion medium, one may obtain a diagnostic agent using the ascites or serum of a patient directly as the specimen to be arranged, without resorting to any complicated procedures. We have also succeeded in the preparation of diagnostic agents which remain stable even after prolonged storage and are least liable to give doubtful positive results and capable of providing an advantageous test for primary hepatoma. This invention is the culmination of the foregoing discovery and development. Many other advantages and features of the instant invention will become apparent as the following description of the invention proceeds.

DETAILED DESCRIPTION OF THE INVENTION

The different embodiments of this invention will now be discussed in greater detail.

1. The following description is directed to the preparation of a diagnostic agent of this invention, wherein the antibody, anti-$\alpha$1-fetoglobulin, is dissolved together with a support medium and the solution is allowed to solidify in a diffused condition.

Thus, this particular diagnostic agent is prepared by using the antigenic $\alpha$1-fetoglobulin to immunize an animal. The resulting anti-serum is dissolved together with a support medium and, if desired, a surfactant, coloring agent, and/or preservative. This solution is allowed to solidify in the diffused condition.

The support medium used in the practice of this invention is one which has a high diffusion coefficient in terms of viscosity. For purposes of discrimination convenience, the medium should be characterized by a satisfactory degree of clarity. Among the media that satisfy the above conditions are agar, dextrin, starch, pectin and other polysaccharides, and various proteins including gelatin and the like. Preferably, agar, synthetic polyacrylamide gel and starch are employed. The surfactant is used in the practice of this invention for the purpose of reducing the percentage of doubtful positives attributable to hypercholesteric sera in clinical applications, and may be selected from the group consisting of anionic surfactants such as sodium oleate, sodium laurylsulfate, sodium octylsulfate, sodium stearyl sulfate, sodium alkylbenzene sulfonate, sodium dialkylsulfosuccinate, etc., cationic surfactants such as dodecylamine acetate, benzyldimethylalkylammonium halide, cetylpyridinium halide, etc., and nonionic surfacants such as polyoxyethylene fatty acid esters, polyoxyethylenesorbitan fatty acid esters, polyoxyethylene (higher) alcohol ethers, polyoxyethylenalkylaryl ethers, polyoxyethylene castor oil derivatives, etc., as well as lecitin, saponin, taurocholic acid and the like. Among the preferred surface active agents which provide particularly beneficial results include polyoxyethylenesorbitan fatty acid esters (Tween type) which are non-ionic. A colorant may be used to facilitate the diagnosis. The colorant may, for example, be Evans blue, toluidine blue, brilliant green, brilliant blue FCF, Alcian blue, patent blue, trypan blue, amido black 10B, or Ponceau 3R. Among those colorants, patent blue and trypan blue are particularly advantageous. A preservative may be added including the various phenolic compounds, such as cresol, chlorothymol, thymol, paraoxybenzoic acid ester, etc.; organic mercury compounds, such as thimerosal, phenylmercury acetate, phenylmecury borate, etc.; chlorobutanol and other alcohols, sodium azide, and the like. The mode of practice of the instant invention will hereinafter be described in detail.

A buffer solution of predetermined pH and ionic strength is prepared for the purpose of stabilizing the diagnostic agent. This buffer solution is preferably a tris-HCl-saline or glycine-sodium chloride buffer, although citrate, phosphate, borate and barbiturate buffers may likewise be employed. The pH of this solution may range from weakly acidic to weakly alkaline; that is to say, from pH 6.5 to pH 8.5. The optimum pH lies somewhere between pH 7.2 to pH 8.2. The above buffer solution is maintained in a container at a temperature of preferably from 50°C. to 56°C., and the support medium is dissolved in the solution. It is preferable that the support medium be added to a final concentration of 1 to 15W/V%.

The anti-serum prepared by the procedures hereinbefore described is dissolved in the same buffer as above to a final concentration of 1 to 10W/V%, and the resulting solution is admixed with the support-buffer solution prepared above. The surface active agent and coloring agent are added to final concentration of 0.01 to 0.20 W/V% and 0.001 to 0.005 W/V%, respectively. When the surfactant used is taurocholic acid, the final concentration should be between 0.2 to 0.5 W/V%. To the thus-prepared composition, the preservative agent is added until a final concentration of 0.1 W/V% is reached. After sufficiently mixing the composition, an aliquot is poured into a suitable vessel, in which it is allowed to solidify. The desired immunodiffusion plate is then obtained by providing wells in the solidified composition, from which the test serum may diffuse. It is to be understood that, in the practice of this invention, the foregoing procedures may be modified within the limits that are obvious to those skilled in the art.

The vessel in which the diagnostic agent of this invention is to be filled and stored must be such that it is transparent throughout and can be hermetically sealed to prevent evaporation of moisture. In addition, the vessel should be of a suitable design to lend itself to easy manipulation. An example of a vessel which satisfies these requirements is a colorless, transparent plastic vessel suitable for containing a level of diagnostic agent up to 2 millimeters. After the foregoing procedures have been carried through, the diagnosis and quantitation, according to this invention, can be conducted with extreme ease, quickly and accurately. Thus, when the serum specimen from a test person is allowed to diffuse on the above immunodiffusion plate, a precipitin ring is specifically formed if antigenic proteins are present. Cases of primary cancers of the liver can thus be recognized by this test. The area of the precipitin ring thus formed is proportional to the quantity of the antigenic proteins and, therefore, the quantitation of the antigen can be determined by the mere determination of the diameter of the ring. Primary hepatoma can be easily detected by using the three preparations of the crude, 10- and 100-fold serums. It is one of the advantages of this technique that since the diagnostic agent obtained in the above-described manner enables the antigen to be quantitated, the progress or stage of the primary hepatoma can be easily determined.

2. The following description relates to the embodiment of this invention wherein the anti-$\alpha$1-fetoglobulin, which is the antibody, is adsorbed on a carrier medium which is then dispersed in a dispersion medium.

To obtain this diagnostic agent, anti-$\alpha$1-fetoglobulin is first adsorbed on a carrier medium which is then dispersed in a dispersion medium. The carrier medium used in this embodiment of the invention may be selected from among the common adsorbents and ion exchange resins, including aluminum-silicate adsorbents, such as kaolin, bentonite, diatomaceous earth, acid clay, etc.; magnesium-aluminum-silicate adsorbents, such as beagum, etc.; silicic anhydride; acrylic resin adsorbents; polystyrene latex; polyvinyltoluene latex; Bioglass (manufactured by Muromachi Chemical Industries, Ltd.); ion exchange resins, such as Amberlite IRA411, IRA93, IR45, IR4B, IRA68, and IRC50 (Rohm & Haas Company); Dowex44 (Dow Chemical Company), and others. Since the above carrier medium exerts an influence on the adsorption and stability characteristics of the diagnostic agent, it is preferably spherical in shape and uniform in grain size. The diameters of the grains are desirably within the range of 0.5 to 3 microns.

To cause anti-$\alpha$1-fetoglobulin to be adsorbed on this carrier medium in accordance with this invention, the carrier medium is first dispersed in a suitable buffer solution and the anti-serum is added to the resulting dispersion, followed by thorough shaking.

For the present purpose, a variety of buffer solutions may be employed. For instance, tris-HCl-saline buffer and sodium chloride-aminoacid buffer and barbiturate buffer, as well as citrate, phosphate and borate buffers can be used to advantage. It is preferable that the above carrier be added in a sufficient amount to give a final concentration of 0.2 to 5 W/V%. The amount of the antiserum depends upon the concentration of anti-$\alpha$1-fetoglobulin. Generally speaking, the anti-serum is previously dissolved in the above buffer to a final concentration of 1 to 10 W/V% and in the case of the purified antibody, it is dissolved in the above buffer to a final concentration of 0.1 to 1 W/V%. The solution is added to the above carrier-buffer, followed by sufficient shaking.

In this manner, the anti-$\alpha$1-fetoglobulin contained in the anti-serum is adsorbed around the carrier to give an anti-$\alpha$1-fetoglobulin-carrier combination.

This anti-$\alpha$1-fetoglobulin-carrier combination is then separated by, for example, centrifugation and, after being washed with, for example, the same buffer solution as above, is dispersed in a dispersion medium. The dispersion medium is desirably one of the above-mentioned buffer solutions. In this connection, a suitable dispersing agent is used to ensure a more uniform dispersion of the anti-$\alpha$1-fetoglobulin-carrier combination and a stabilized maintenance of anti-$\alpha$1-fetoglobulin in adsorbed condition.

The dispersing agent mentioned above is desirably selected from among albumin, peptone, gelatin, agar, saponin, alginic acid, polyvinylpyrrolidone, polyphosphoric acid, serum and the like. Aside from those dispersing agents, various surface active agents may be employed. Sufficient effects may be achieved by using such an agent in a proportion of from 0.1 to 1 W/V%.

For added ease of diagnosis, a coloring agent may be incorporated into the diagnostic agent. Suitable coloring agents include those colors mentioned above and particularly patent blue and trypan blue provide satisfactory results.

Because the diagnostic agent of this invention is, in many cases, subjected to prolonged storage, it is advantageous to incorporate a small amount of a preservative such as those specified above.

It is to be noted that the anti-$\alpha$1-fetoglobulin-carrier combination is dispersed desirably to a final concentration of 0.5 to 5W/V% and, at the last stage, the dispersion is adjusted to pH 6.5 – 8.5 and, for the best result, to pH 8.2 – 8.5.

The diagnostic agnet thus obtained is superior to that prepared by dissolving the same anti-serum together with a support medium and allowing the same to solidify in a diffused state, since it enables diagnosis in a shorter period of time. Regardless of the diagnostic agent, however, in order to increase the sensitivity of the agent to detection of disease and to lower the incidence of false positive results and establish a high reliability as to quantitation, it is important to obtain a purified grade of anti-$\alpha$1-fetoglobulin. To this end, the impurities should be removed as much as possible from the ascites or serum of the patient suffering from a primary hepatoma, or from fetal serum.

3. The following explanation is relevant to the case wherein the ascites or serum from a patient having a primary hepatoma, or fetal serum is used to immunize an animal, which is then bled, the serum is separated from the blood sample and the resulting anti-serum is absorbed into normal human serum.

The ascites or serum obtained from a patient suffering from a primary hepatoma or serum from a fetus is added to, for example, an equal amount of physiological saline, followed by the addition of an equal amount of Freund's complete adjuvant (manufactured by Difco). After being emulsified, the system is used to immunize an animal. The animal may be, for example, a rabbit, a horse or an ox. Particularly benefical is a method wherein a rabbit is subcutaneously injected in a foot pad. Injections are repeated at timed intervals and after a sufficient gain has been confirmed in antibody titer, the animal is bled and the serum is separated. The resulting antiserum is absorbed with normal human serum or with the abovementioned insoluble immunoabsorbent to obtain a specific antiserum.

This antiserum is desirably high in anti-$\alpha$1-fetoglobulin concentration in order to increase the sensitivity of detection of the disease in question and to lower the incidence of false positive results. Therefore, better results are obtained if the above antiserum is purified by, for example, ammonium sulfate fractionation.

Since the ascites or serum of a patient having a primary hepatoma, or fetal serum contains various serum proteins, such as albumin, $\gamma$-globulin, etc., in addition to $\alpha$1-fetoglobulin, when animals are immunized with the ascites or serum as such, anitbodies are found which correspond to those various serum proteins in addition to anti-α1-fetoglobulin. It is therefore necessary to absorb this antiserum with a large quantity of normal human serum. However, the anti-α1-fetoglobulin obtained in this stage has already been highly purified and can be directly dissolved along with a support medium or, alternatively, dispersed in a dispersion medium after being adsorbed on a carrier medium to prepare a satisfactory diagnostic agent.

Preferably, however, the antiserum after the absorption step is further purified.

4. The following description is directed to the mode of practice, in which the ascites or serum of a patient having a primary hepatoma, or fetal serum, is first purified by a protein fractionation technique and the resulting α1-fetoglobulin fraction is used to immunize an animal which is then bled, followed by separation of the serum from the blood sample thus collected. Thus, the ascites or serum obtained from a patient suffering from a primary hepatoma, or fetal serum, is purified by a conventional serum protein fractionation technique. Suitable known fractionation techniques include Cohn's fractionation method, Spiro's modified method, ammonium sulfate fractionation (salting-out), gel filtration, column chromatography, isoelectric fractionation, electrophoresis, membrane filtration and the like, which techniques may be employed either singly or in combination.

The thus-obtained α1-fetoglobulin fraction is dissolved in, for example, an equal amount of physiological saline solution, followed by the addition of Freund's complete adjuvant (Difco) to emulsify the same. The animal is then immunized with the above emulsion. Suitable animals for this purpose include such species as rabbits, goats, cattle and horses. Particularly preferred are rabbits, whose foot pads are choice sits for subcutaneous innoculation. Injections are repeated at suitable intervals, with the gain in titer of the antibody being traced constantly. When the antibody titer is at the maximum, the ear vein is punctured to collect blood samples every other day. The antibody titer reaches its peak value in about 1 to 2 weeks after injection. The serum is separated and absorbed with a small amount of normal human serum or its gel is used to obtain the desired anti-α-1-fetoglobulin.

In the practice of this invention, as has hereinbefore been described, only a very small amount of normal human serum is required to absorb the antiserum. For instance, when the serum has not been purified, it is necessary to use at least equal amounts of normal human serum and antiserum. In contrast, in the method of this invention, 0.1 to 0.35 of normal human serum is required per part of antiserum. Furthermore, the antibody titer of the antiserum obtained by the method of this invention, as arranged against the standard antigen, is 2 to 8 times as high as that of the crude antiserum.

By the afore-described procedures, a high degree of purification can be accomplished. In addition, the method of this invention avoids many of the disadvantages of the prior art. Thus, the use of a large quantity of normal human serum was not only commercially disadvantageous, but was also liable to result in a reduction in antibody titer caused by coprecipitation of anti-α1-fetoglobulin. In addition, the prior art procedures were not sufficient to overcome the difficulty of absorbing anti-α2-macroglobulin and analogous substances. In contradistinction, this invention makes it feasible to obtain a high grade of antiserum with the use of extremely small amounts of normal human sera. Furthermore, there is substantially no contamination with anti-α2-macroglobulin and analogous substances. A further striking fact is that the antibody titer of the antiserum obtained by the present method is by far higher than that obtainable by the conventional procedure referred to above. The anti-α1-fetoglobulin serum which has thus been prepared is then either dissolved in a buffer solution together with a support medium or adsorbed on a carrier medium and dispersed in a dispersion medium, whereby an excellent diagnostic agent is prepared.

The purposes of the present diagnostic agent can generally be fully achieved by using the anti-α1-fetoglobulin obtained in the foregoing manner. However, when it is desired to obtain an unusually high grade of the diagnostic agent, for example, for academic purposes, it becomes necessary to purify the α1-fetoglobulin to an extreme degree of purity. Procedures that will be necessary for the preparation of such high grades of α1-fetoglobulin also fall within the purview of the instant invention.

We will now describe the purification technique wherein the ascites or serum obtained from a patient having a primary hepatoma, or serum from a human fetus, is dialyzed against acrinol and the precipitate arising from the dialyzate is purfied by the action of a protein fraction. Thus, the ascites or serum from a patient having a primary hepatoma, or human fetal serum, is diluted with water to 3 – 5 times the initial volume and dislyzed against an aqueous solution of 0.1 –0.01 W/V% acrinol. The dialysis is desirably carried out against acrinol and the serum or ascites as an internal phase for about 24 hours.

This acrinol solution is then centrifuged or otherwise treated to obtain a sediment which is a fairly purified grade of α1-fetoglobulin. However, since this sediment also contains small amounts of impurities, including albumin, it can be fractionated by conventional protein fractional purification techniques to obtain a purified grade of α1-fetoglobulin.

Among the applicable protein-fractionation-purification techniques are ammonium sulfate fractionation, dialysis, column chromatography, membrane filtration, isoelectric fractionation and other techniques, which may be practiced either singly or, if necessary, in combination. The best possible result may be obtained by the following procedures.

The aforementioned sediment is first dissolved in, for example, a physiological saline solution or a buffer solution and after the insoluble matter is removed, the solution is dialyzed against a buffer solution (ionic strength: 0.03 to 0.4 M and pH 4.5 to 5.5). The buffer solution may, for example, be acetate buffer, tri-HCl-saline buffer, sodium chloride-glycine buffer citrate, phosphate or borate buffer. The dialyzate is then run into a colunm or carboxymethyl-cellulose column (ionic strength 0.03 – 0.04 M; pH 4.5 – 5.5) and eluted from 0.03 – 0.4M to 0.2M. In this manner, the desired α1-fetoglobulin is eluted from the column, starting at about 0.055M. The resulting fractions are pooled and a pure grade of α1-fetoglobulin is obtained. Aside from carboxymethyl-cellulose, the above column chromatography may likewise be carried out on such other materials as DEAE-celluslose, TEAE-celluslose and the like. This column chromatography is desirably conducted in repetition, i.e., two or more times, at least one of which being on carboxymethyl-cellulose.

Since the above procedures yield a substantially pure form of α1-fetoglobulin, almost completely free of contaminant proteins, this method is the most suitable antigen purification method ever conceived where an extremely high purity academic research grade of α1-fetoglobulin is required for the preparation of the present diagnostic agent.

The material α1-fetoglobulin is preferably high in purity for preparation of the present diagnostic agent, since if a grade of α1-fetoglobulin contains a fairly large amount of impurities, it is necessary to remove the antibodies corresponding to those contaminants in the course of production of the diagnostic agent. This removal not only involves complicated procedures but also leads to considerable reductions in product yields.

The following methods are known for the collection and purification of α1-fetoglobulin 1. Bergstrand and Czar used fetal sera as the raw material and fractionated the same electrophoretically. They found α1-fetoglobulin in a location which coincides with that of albumin and reported that they had noted a slight difference in molecular weight as determined by the ultracentrifugation technique [Scand. J. Clin. & Lab. Invest., Vol. 9, p.227 (1957)].

2. Davis, et al. passed umbilical sera twice through a column of Sephadex G-200 and eluted the same with 0.1M aqueous solution of sodium chloride. It was reported that they had noticed the concentration peak of α1-fetoglobulin in the fraction coincidental with those of transferrin and albumin. [J. Clin. Invest., 45 (1966)].

3. Hirai et al. caused fetal sera to be adsorbed on a column of DEAE-cellulose (pH 5.5, 0.02 M) and conducted a gradient elution against 0.2M, whereupon α1-fetoglobulin was eluted as the shoulder of an albumin peak. This fraction was then adsorbed on a column of CM-cellulose (pH 4.8 and 0.2M) and a gradient elution conducted against 0.5M. As a result, they obtained three peaks, of which α1-fetoglobulin was the third. The latter half of this peak was rechromatographed to obtain a single peak for α1-fetoglobulin. (Reported before the Society Of Electrophoretic Researchers on October 1, 1969.)

Those reports, however, went no further than to confirm the existence of α1-fetoglobulin or the production of α1-fetoglobulin in a crude form, and these methods are not conducive to the obtaining of high grades of α1-fetoglobulin.

Nevertheless, insofar as it is to be used as the raw material for a diagnostic agent for primary hepatoma in academic research applications, α1-fetoglobulin must be of particularly high purity, since its purity has an important influence upon the accuracy of the diagnostic agent.

In view of the foregoing, we conducted extensive studies to obtain a highly pure grade of α1-fetoglobulin and, particularly, to develop a method for positively removing the contaminant albumin at low cost. Those studies have ultimately led to the finding that a pure grade of α1-fetaglobulin can be obtained by first dialyzing sera or other materials containing α1-fetaglobulin against acrinol and then fractionating the dialyzate by procedures which are conventionally followed for fractional purification of proteins. The instant invention is the culmination of the above finding and affords an extremely useful method for the preparation of a high grade of α1-fetaglobulin without resorting to complicated procedures.

Clinical data pertinent to the use of the diagnostic agents of this invention are given below.

Of the diagnostic agents for primary hepatoma according to this invention, the clinical results for diagnosing primary hepatoma with the use of the diagnostic agents of the present invention using a support medium are set forth in Table 1. There were a total of 63 cases, most of which were diagnosed at the National Cancer Center Hospital, including both in and out-patients. Of these, 12 were primary hepatocarcinomatous cases (of which 11 cases were established by tissue diagnosis), 15 were metastatic hepatocarcinomatous cases, 15 were hepato-cirrhosis cases, 22 were hepatitis cases, and 1 was a hepatangiomatous case. The antigen quantitation reslults for the positive cases which showed precipitin rings in the present array and the results obtained by the conventional diagnostic technique are set forth in Table 2.

TABLE 1

| Diseases | Number of Cases Diagnosed | Number of Positive Cases |
|---|---|---|
| Primary hepatocarcinoma | 12 | 11 |
| Metastatic hepatocarcinoma | 15 | 0 |
| Hepatocirrhosis | 15 | 0 |
| Hepatitis | 22 | 0 |
| Hepatoangioma | 1 | 0 |

TABLE 2

| Name of Patient, Initials Only | Age | Sex | Antigen (u/ml)*** | Results By Conventional Method** |
|---|---|---|---|---|
| Y.Y. | 23 | Male | 1,600 | + |
| M.T. | 65 | Female | 9 | − |
| S.W. | 60 | Female | 11 | + |
| N.S. | 58 | Male | 150 | + |
| S.H. | 8 | Male | [ 15,000 * | [+ |
|  |  |  | [ 1,050 | [+ |
| M.S. | 12 | Male | 1,000 | + |
| K.W. | 65 | Male | 2,826 | + |
| H.A. | 19 | Male | 5 | − |
| K.M. | 62 | Male | 300 | + |
| B.I. | 62 | Male | 1,300 | + |
| S.Y. | 3 | Male | 130 | + |

*Ascite was used: Sera was used in the other cases.
**Ouchterlony's method
***U/Ml = 0.3 δ/ml.

It will be seen from the above Table that in those cases which were diagnosed positive with the diagnostic agent of this invention, the conventional diagnostic method failed to identify the disease when the antigen titers were less than 10 μ/ml.

For the diagnosis of primary hepatoma using a diagnostic agent prepared with a carrier medium, the following simple procedure was used. A drop of the diagnostic agent was placed on a slide glass, where a fresh sample of serum was mixed with the diagnostic agent. When this admixture occurs, a specific agglutination reaction occurs if the patient has a primary hepatoma. As will be seen from the following clinical data, comparison of this particular diagnostic agent and the previously-described diagnostic agents prepared with use of a support medium reveals that all the primary hepatoma prove positive, irrespective of whether sera or ascites are employed.

termined spaced intervals and the resulting preparation is used as an immunological agar plate.

EXAMPLE 2

To sodium chloride-glycine buffer (pH 8.2) is added an immunological refined grade of agar to a final concentration of 1.0 W/V%, followed by heating to 50°C. Separately, horse antiserum is added to the same buffer as above in a sufficient amount to give a final concentration of 4 W/V%, followed by heating to 50°C. The two solutions are mixed, and sodium taurocholate is added in a sufficient amount to give a final concentration of 0.3%. Trypan blue and chlorobutanol are then

| Name Of Patient, Initials Only | Sample Arranged | This Method | Support Method Dia. of Band. mm. | Dilution factor, times |
|---|---|---|---|---|
| M.S. | Serum | ++ | 6.0 | X8 |
| S.Y. | " | ++ | 5.7 | X8 |
| C.Y. | " | + | 4.0 | Original serum |
| Y.S. | " | + | 4.2 | Original serum |
| K.N. | " | ++ | 6.2 | X8 |
| K.Y. | " | + | 4.0 | Original serum |
| A.S. | " | ++ | 7.3 | X8 |
| N.S. | " | ++ | 6.0 | X8 |
| E.S. | Ascites | +++ | 12.3 | X8 |
| S.Y. | " | ++ | 7.5 | X8 |
| Normal Human | Serum | − | 0.0 | |

(Note 1)
The above data were obtained at the National Cancers Center.
(Note 2)
The designations of results in the Table are: −negative: +weakly positive: ++positive and +++strongly positive.

Having now generally described the invention, a better understanding can be obtained by reference to certain specific Examples which are provided herein for purposes of illustration only and are not intended to be limiting in any manner.

PREPARATION OF THE DIAGNOSTIC AGENTS WITH A SUPPORT MEDIUM

EXAMPLE 1 added to the above system until the final concentrations are 0.002% and 0.3%, respectively. After the additives are dispersed, the system is poured into a vessel. After the system has solidified, wells are bored therein to obtain an immunological agar plate.

Sodium chloride is added to Tris- or amino acid buffer (pH 6.5 – 8.5) to prepare an isotonic solution, and the following materials are added until the designated final concentrations are reached.

| Sample No. | Support Medium | Final conc., % | Surfactant | Final conc., % | Coloring Agent | Final Conc., % | Preservative | Final Conc., % |
|---|---|---|---|---|---|---|---|---|
| 3 | Synthetic 1.5 polyacrylamide gel | 1.5 | Sodium oleate | 0.1 | Brilliant Green | 0.002 | Thymol | 0.1 |
| 4 | Pectin | 1.3 | Alkyltrimethyl-ammonium bromide | 0.05 | Patent Blue | 0.001 | Phenylmercury acetate | 0.02 |
| 5 | Dextrin | 1.5 | Polyoxyethylene-sorbitan monolaurate | 0.1 | Alcian Blue | 0.003 | Sodium nitride | 0.1 |
| 6 | Starch | 1.0 | Saponin | 0.03 | Trypan Blue | 0.001 | Phenylmercury borate | 0.01 |
| 7 | Agar | 1.2 | Sodium myristyl sulfate | 0.15 | Brilliant Blue | 0.004 | Thimerosal | 0.01 |

To tris-HCl-saline buffer (pH 7.2) is added a refined immunological grade of agar to a final concentration of 1.5%. The mixture is heated, and the agar is completely dissolved. This solution is maintained at a temperature of 55°C. Separately, rabbit antiserum is absorbed with 0.35 parts of normal human serum to make a final concentration of 3 W/V% which is mixed with the agar support prepared above. Tween 80, patent blue and sodium azide are added in sufficient amounts to provide a final concentration of 0.01%, 0.001%, and 0.1%, repectively. After those additives are well dispersed, the system is poured into a pre-warmed container to a depth of 1 millimeter. After the system has solidified, wells, 3 millimeters in diameter, are formed at prede-

PREPARATION OF THE DIAGNOSTIC AGENT WITH A CARRIER MEDIUM

EXAMPLE 8

1.5g. of crushed, purified Amberlite IR45 (1-3 μ in size) is dispersed into 10 milliliters of sodium chloride-glycine buffer solution (pH 8.2), followed by the addition of an optimal amount of anti α1-fetoglobulin serum. The system is shaken at 4°C. for 2 hours, whereby the anti-α1-fetoglobulin is adsorbed onto the carrier medium. The sediment Amberlite IR45 coated with the anti-α1-fetoglobulin is centrifuged twice, using the same buffer solution as above to which 0.3 W/V% albumin and 0.1 W/V% sodium azide have been added. After washing, the carrier anti-α1-fetoglobulin is dispersed in about 90 ml. of the same buffer solution and is brought to an exact pH of 8.2. An additional volume of the same buffer is added so that a total volume of 100 ml. is reached.

EXAMPLE 9

1.5g. of crushed, purified Amberlite IRA 411 the size of 1 to 3 $\mu$ is dispersed in 5 ml. of tris-HCl-saline buffer solution (pH 8.2), followed by the addition of an optimal amount of fractionated anti-$\alpha$1-fetoglobulin and 0.01g. patent blue. The system is shaken at 4°C. for 2 hours, whereby the anti-$\alpha$1-fetoglobulin is adsorbed. The system is centrifuged and the resulting anti-$\alpha$1-fetoglobulin-amberlite IRA411 is centrifuged twice, using the same buffer solution as above to which 0.5 W/V% of normal rabbit serum and 0.1 W/V% sodium azide have been added. After washing, the sediment is dispersed in about 90 ml. of the same buffer solution as above and brought to an exact pH value of 8.5. An additional volume of the same buffer solution is used to make up the dispersion to a total volume of 100 ml.

EXAMPLE 10

0.25g. of polystyrene latex the size of 0.8 $\mu$ is dispersed in 8 ml. of sodium chloride-phosphate buffer solution (pH 8.5) followed by the addition of an optimal amount of anti-$\alpha$1-fetoglobulin serum. The system is shaken at 37°C. for 1 hour, whereby the anti-$\alpha$1-fetoglobulin is adsorbed onto the carrier medium. The system is centrifuged and the resulting anti-$\alpha$1-fetoglobulin-latex is centrifuged twice, using the same buffer as above to which 0.1 W/V% sodium azide has been added. After washing, the anti-$\alpha$1-fetoglobulin-latex is dispersed in about 90 ml. of the same buffer solution as above and the dispersion brought to pH 8.5. An additional volume of the same buffer is used to make up the dispersion to a total volume of 100 ml.

EXAMPLE 11

Kaolin is purified by fractional precipitation to the size range of 1 to 3 $\mu$ and 2 grams of the purified kaolin is dispersed in 10 ml. of sodium chloride-borate buffer solution, followed by the addition of an optimal amount of anti-$\alpha$1-fetoglobulin and 0.01g. brillant blue FCF. The system is shaken at 4°C. for 2 hours, whereby the anti-$\alpha$1-fetoglobulin is adsorbed on the kaolin. The anti-$\alpha$-fetoglobulin-kaolin is washed twice in the same buffer solution to which 0.5 W/V% Tween 80 and 0.01 W/V% thimersal have been added. To this system is further added about 90 ml. of the same buffer as above so that the pH of the system if 6.5. Finally, an additional amount of the same buffer is used to make up the system to a total volume of 100 ml.

PREPARATION OF ANTI-$\alpha$1-FETOGLOBULIN

EXAMPLE 12

To a part (by weight) of the serum of a patient having a primary hepatoma is added by dissolution is ethanol. The 28 V/V% ethanolic solution is adjusted to pH 6.4 and allowed to stand at −5°C. for 14 hours. The solution is centrifuged and the supernatant liquid is removed. A 0.02M solution of barium acetate is added to the supernatant liquid and the mixture is made into a 25 V/V% ethanolic solution, which is adjusted to pH 6.7. The solution is allowed to stand at −5°C. for 2 hours, at the end of which time it is centrifuged. The supernatant is made into a 40 V/V% ethanolic solution which is further allowed to stand at −5°C. for 2 hours. The solution is centrifuged and the supernatant is made into a 40 V/V% ethanolic solution which is left standing at −10°C. for 14 hours, at the end of which time the resulting precipitate is recovered. The precipitate is dissolved in a solution of sodium citrate and the solution is dialyzed against water at 4°C. for a few days, at the end of which time the dialyzate is lyophilized to obtain the antigen.

A predetermined amount of this antigen is used to immunize rabbits by the complete adjuvant method and when the antigen titers have reached the desired level, the rabbits are bled and the sera separated. To those sera is added 0.2 volume of normal human serum and the mixture is allowed to stand at 37°C. for 1 hour and, then, at 4°C. overnight. The system is then centrifuged to obtain the desired anti-$\alpha$1-fetoglobulin serum.

The same procedure as mentioned above is conducted except using an immunoadsorbent instead of human serum to obtain the same result.

The immunoadsorbent is prepared as follows 10 ml. of the normal human serum is adjusted to pH 5.5 with an acetate buffer solution. There is added 1.0 ml. of glutaraldehyde and the solution is allowed to stand for 3 hours. After adding a phosphate buffer solution, the solution is centrifuged and the precipitants collected.

The precipitants are washed with the above buffer solution several times and suspended with the above buffer solution.

EXAMPLE 13

To 1 part of the serum of a patient is added 1 part of 0.1M sodium chloride-phosphate buffer solution (pH 7.2), followed by the gradual addition of 2 parts of a saturated aqueous solution of ammonium sulfate while stirring, whereupon a precipitate is formed. The system is allowed to stand overnight at 4°C. and is then centrifuged at 8,000 r.p.m. for 20 minutes. The supernatant is dialyzed against water at 4°C. for a few days, at the end of which time the dialyzate is lyophilized to obtain the desired antigen.

This antigen was used to immunize a goat, followed by the same treatments as described in Example 12. The resulting antiserum was absorbed with 0.35 volume of normal human serum to obtain the desired anti-$\alpha$1-fetoglobulin serum.

EXAMPLE 14

A 5 milliliter sample of the ascites of a patient having a primary hepatoma is run into a column (3 × 100 cm.) of Sephadex G-200, which is then eluted with 0.1M tris-HCl-saline buffer (pH 8.0) at the rate of 20 to 25 ml./hour. The fractions which correspond to $\gamma$-globulin (second peak) to albumin (third peak) are arranged by Ouchterlony's method to confirm the $\alpha$1-fetoglobulin fraction, which is collected. This fraction is dialyzed using water as an external phase at 4°C. for a few days and the dialyzate is concentrated under suction using a collodione bag to obtain the desired antigen.

This antigen is used to immunize rabbits, followed by treatments similar to those described in Example 12. The resulting antiserum is absorbed with 0.2 volume of normal human serum to obtain the required anti-$\alpha$1-fetoglobulin serum.

EXAMPLE 15

The antigen obtained according to Example 14 is further purified by means of an isoelectric fractionation apparatus. Thus, the antigen is run onto a sucrose-gradient column containing 0.5 V/V% carrier ampholyte of pH 3 – 10. While the column is maintained at 4°C., a current of 700 volts is applied for 2 days. After this separation, the fractions of pH 4.2 to 4.5 are pooled and dialyzed at 4°C. for a few days, using water as the external fluid. The dialyzate is then concentrated under suction using a collodione bag to obtain the desired antigen.

This antigen was used to immunize rabbits, which were treated in the same manner as in Example 12. The resulting antiserum is absorbed with 0.1 volume of normal human serum to obtain the desired anti-$\alpha$1-fetoglobulin serum.

EXAMPLE 16

A 50 ml. sample of the ascites of a patient having a primary hepatoma is diluted with water to 4 times its initial volume and the diluted sample is dialyzed against 5 liters of 0.1 W/V% solution of acrinol for 24 hours. The acrinol solution is centrifuged at 4,000 r.p.m., and the sediment is dissolved by shaking in 50 ml. of physiological saline solution. The solution is centrifuged a second time at 4,000 r.p.m. The supernatant liquid is dialyzed against an acetate buffer solution (ionic strength 0.04, pH 5.0) and the dialyzate is run into a column of carboxymethyl-cellulose (pH 5.0, ionic strength 0.04), which is eluted to 0.2M. Since $\alpha$1-fetoglobulin starts eluting at about 0.055M, this fraction is collected. The above procedure is repeated twice to obtain a single $\alpha$1-fetoglobulin fraction.

Whereas the $\alpha$1-fetoglobulin titer of the original ascites is 3146 U/ml. (50 ml.), the final titer is 600 U/ml. (200 ml.) which represents a recovery of 70 W/V%. Since the original amount of albumin was 7.623 mg./ml., (50 ml.), it is impossible to detect the same with the immuno-plate at the final stage.

EXAMPLE 17

A 50 ml. sample of the ascites of a patient having a primary hepatoma is diluted with water to 4 times its original volume and dialyzed against 5 liters of 0.05W/V% solution of acoinol for 24 hours. The dialyzate is centrifuged at 3,000 r.p.m. and the sediment is dissolved by shaking in 50 ml. of physiological saline solution. The solution is centrifuged a second time at 3,000 r.p.m. The supernatant liquid is dialyzed against tris-HCl-saline buffer (0.03M, pH 4.5) and the dialyzate is run onto a column of DEAE-cellulose (pH 4.5, ionic strength 0.04) and eluted to 0.2M. The eluate is similarly treated with a column of CM-cellulose to obtain a single $\alpha$1-fetoglobulin fraction.

Whereas the $\alpha$1-fetoglobulin titer of the original ascites is 2,500U/ml. (50ml.), the final titer is 400U/ml. (180 ml.), which represents a recovery of 60 W/V%.

Incidentally, while the original amount of albumin is 7.915 mg./ml., it is impossible to detect it with the immuno-plate at the final stage.

Having now fully described the invention, it will be apparent to one of ordinary skill in the art that many changes and modifications can be made thereto without departing from the spirit or scope of the invention.

Accordingly, what is claimed and intended to be covered by Letters Patent of the United States is:

1. A process for the preparation of anti-$\alpha_1$-fetoglobulin which is used for the preparation of a diagnostic agent for primary hepatoma which comprises:
   a. purifying the ascites from a patient having a primary hepatoma by means of gel filtration chromatography;
   b. dialyzing the $\alpha_1$-fetoglobulin fraction obtained from purifying step (a) so as to obtain $\alpha_1$-fetoglobulin;
   c. immunizing animals with said $\alpha_1$-fetoglobulin of step (b);
   d. bleeding said immunized animals;
   e. separating an anti-$\alpha_1$-fetoglobulin-containing serum from the blood of said bled animals; and
   f. absorbing said serum with normal human serum or insoluble normal human serum immunoabsorbent.

2. The process of claim 1, wherein said $\alpha_1$-fetoglobulin of step (b) is further purified by means of isoelectric fractionation.

3. A process for the preparation of anti-$\alpha_1$-fetoglobulin which is used for the preparation of a diagnostic agent for primary hepatoma which comprises:
   a. purifying the ascites from a patient having a primary hepatoma by means of dialysizing an aqueous solution of said ascites in a ratio of 3–4:1 water to ascites against an aqueous solution of 0.1 – 0.01 W/V% acrinol;
   b. purifying the precipitate formed in step (a) by means of isoelectric fractionation or gel filtration chromatography to obtain the $\alpha_1$-fetoglobulin;
   c. immunizing animals with said $\alpha_1$-fetoglobulin of step (b);
   d. bleeding said immunized animals;
   e. separating an anti-$\alpha_1$-fetoglobulin-containing serum from the blood of said bled animals; and
   f. absorbing said serum with normal human serum or insoluble normal human serum immuno-absorbent.

4. The process of claim 3, wherein said acrinol is a 0.05% aqueous solution.

* * * * *

UNITED STATES PATENT OFFICE
CERTIFICATE OF CORRECTION

Patent No. 3,946,105　　　　　　　　Dated March 23, 1976

Inventor(s) Hidetaka Nagai et al.

It is certified that error appears in the above-identified patent and that said Letters Patent are hereby corrected as shown below:

The Title should read as follows:

-- Preparation Of Anti-Alpha-Fetoglobulin --.

Signed and Sealed this eighth Day of June 1976

[SEAL]

Attest:

RUTH C. MASON
Attesting Officer

C. MARSHALL DANN
Commissioner of Patents and Trademarks